United States Patent
Schoenle (10) Patent No.: US 10,898,214 B2
(45) Date of Patent: Jan. 26, 2021

(54) SYSTEMS, METHODS AND DEVICES FOR PROGRESSIVELY SOFTENING MULTI-COMPOSITIONAL INTRAVASCULAR TISSUE

(71) Applicant: Cardiovascular Systems, Inc., St. Paul, MN (US)

(72) Inventor: Victor L. Schoenle, Greenfield, MN (US)

(73) Assignee: Cardiovascular Systems, Inc., New Brighton, MN (US)

(*) Notice: Subject to any disclaimer, the term of this patent is extended or adjusted under 35 U.S.C. 154(b) by 279 days.

(21) Appl. No.: 15/859,961

(22) Filed: Jan. 2, 2018

(65) Prior Publication Data

US 2019/0000491 A1    Jan. 3, 2019

Related U.S. Application Data

(60) Provisional application No. 62/441,796, filed on Jan. 3, 2017.

(51) Int. Cl.
| | | |
|---|---|---|
| *A61B 17/22* | (2006.01) | |
| *A61M 25/10* | (2013.01) | |
| *A61B 17/00* | (2006.01) | |

(52) U.S. Cl.
CPC ..... *A61B 17/22012* (2013.01); *A61M 25/104* (2013.01); *A61M 25/10182* (2013.11); *A61M 25/10184* (2013.11); *A61B 2017/00154* (2013.01); *A61B 2017/22001* (2013.01); *A61B 2017/22062* (2013.01)

(58) Field of Classification Search
CPC .... A61B 17/22012; A61B 2017/22001; A61B 2017/22051; A61B 2017/22062; A61B 2017/00154; A61M 25/104; A61M 25/1018; A61M 25/10184; A61M 25/10187

See application file for complete search history.

(56) References Cited

U.S. PATENT DOCUMENTS

| | | | |
|---|---|---|---|
| 5,152,776 A * | 10/1992 | Pinchuk | A61M 25/10184 604/920 |
| 5,486,192 A | 1/1996 | Walinsky et al. | |
| 5,609,606 A | 3/1997 | O'Boyle | |
| 5,722,979 A | 3/1998 | Kusleika | |
| 2007/0197963 A1 | 8/2007 | Griffiths | |

OTHER PUBLICATIONS

International Preliminary Report on Patentability, issued in related PCT application No. PCT/US2018/12128, dated Jul. 18, 2019.
International Search Report and Written Opinion, dated Mar. 23, 2018, for PCT Application No. PCT/US18/12128, filed Jan. 3, 2018.

* cited by examiner

*Primary Examiner* — Melanie R Tyson
(74) *Attorney, Agent, or Firm* — Barnes & Thornburg LLP; Jeffrey R. Stone (57) ABSTRACT

Various embodiments of the systems, methods and devices are provided comprising angioplasty to break up calcification or other tissue in occlusive areas within a blood vessel. The various embodiments disclosed include pressure pulse periods designed to break up calcified occlusive material through a cyclically stretching of the vessel walls without damaging the vessel wall tissue.

16 Claims, 5 Drawing Sheets

SYSTEMS, METHODS AND DEVICES FOR PROGRESSIVELY SOFTENING MULTI-COMPOSITIONAL INTRAVASCULAR TISSUE

CROSS-REFERENCE TO RELATED APPLICATIONS

This application claims the benefit of U.S. Provisional Application No. 62/441,796, filed Jan. 3, 2017 and entitled SYSTEMS, METHODS AND DEVICES FOR STRESS SOFTENING MULTI-COMPOSITIONAL INTRAVASCULAR TISSUE

STATEMENT REGARDING FEDERALLY SPONSORED RESEARCH OR DEVELOPMENT

Not Applicable

BACKGROUND OF THE INVENTION

Field of the Invention

The invention relates to systems, devices and methods for breaking up calcified lesions in an anatomical conduit. More specifically, specific incremental pressure increases are provided to a balloon within a calcified conduit, e.g., a blood vessel, to break the calcified material while not damaging the tissue of the vessel wall.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Angioplasty, or balloon angioplasty, is an endovascular procedure to treat by widening narrowed or obstructed arteries or veins, typically to treat arterial atherosclerosis. A collapsed balloon is typically passed through a pre-positioned catheter and over a guide wire into the narrowed occlusion and then inflated to a fixed size. The balloon forces expansion of the occlusion within the vessel and the surrounding muscular wall until the occlusion yields from the radial force applied by the expanding balloon, opening up the blood vessel with a lumen inner diameter that is similar to the native vessel in the occlusion area and, thereby, improving blood flow.

The angioplasty procedure does present some risks and complications, including but not limited to: arterial rupture or other damage to the vessel wall tissue from over-inflation of the balloon catheter, the use of an inappropriately large or stiff balloon, or the presence of a calcified target vessel; and/or hematoma or pseudoaneurysm formation at the access site. As described above, the primary problem with known angioplasty systems and methods is that the occlusion yields over a relatively short time period at high stress and strain rate, often resulting in damage or dissection of the conduit, e.g., blood vessel, wall tissue.

Currently, the best way to deal with the high stress strain of blood vessel, e.g., artery, wall tissue adjacent to calcified occlusions is to use an atherectomy system marketed by Cardiovascular Systems, Inc., ("CSI") assignee of the instant application. This system comprises an abrasive crown mounted on the drive shaft, wherein the abrasive crown is "eccentric," i.e., with a center of mass located radially away from the drive shaft's axis of rotation. This eccentric (or non-concentric) crown sands and removes calcium internal to the intimal layer of the subject vessel wall in combination with impact energy from the orbiting rotational eccentric crown which works to break and/or soften the embedded calcified plaque.

The CSI atherectomy system and method typically increases the compliance of the calcified occlusion. This is confirmed by balloon inflations requiring lower inflation pressures post atherectomy procedure than non-atherectomy cases. However, the CSI atherectomy system and method may still the use of an adjunctive dilatation balloon to improve lumen diameter gain at the occlusion when there is calcium present within the intimal wall, i.e., not located within the vessel lumen.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 6,295,712, "ROTATIONAL ATHERECTOMY DEVICE";

U.S. Pat. No. 6,494,890, "ECCENTRIC ROTATIONAL ATHERECTOMY DEVICE";

U.S. Pat. No. 6,132,444, "ECCENTRIC DRIVE SHAFT FOR ATHERECTOMY DEVICE AND METHOD FOR MANUFACTURE";

U.S. Pat. No. 6,638,288, "ECCENTRIC DRIVE SHAFT FOR ATHERECTOMY DEVICE AND METHOD FOR MANUFACTURE";

U.S. Pat. No. 5,314,438, "ABRASIVE DRIVE SHAFT DEVICE FOR ROTATIONAL ATHERECTOMY";

U.S. Pat. No. 6,217,595, "ROTATIONAL ATHERECTOMY DEVICE";

U.S. Pat. No. 5,554,163, "ATHERECTOMY DEVICE";

U.S. Pat. No. 7,507,245, "ROTATIONAL ANGIOPLASTY DEVICE WITH ABRASIVE CROWN";

U.S. Pat. No. 6,129,734, "ROTATIONAL ATHERECTOMY DEVICE WITH RADIALLY EXPANDABLE PRIME MOVER COUPLING";

U.S. patent application Ser. No. 11/761,128, "ECCENTRIC ABRADING HEAD FOR HIGH-SPEED ROTATIONAL ATHERECTOMY DEVICES";

U.S. patent application Ser. No. 11/767,725, "SYSTEM, APPARATUS AND METHOD FOR OPENING AN OCCLUDED LESION";

U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE";

U.S. patent application Ser. No. 12/388,703, "ROTATIONAL ATHERECTOMY SEGMENTED ABRADING HEAD AND METHOD TO IMPROVE ABRADING EFFICIENCY";

U.S. patent application Ser. No. 13/624,313, "ROTATIONAL ATHERECTOMY DEVICE WITH ELECTRIC MOTOR";

U.S. patent application Ser. No. 14/315,774, "DEVICES, SYSTEMS AND METHODS FOR LOCALLY MEASURING BIOLOGICAL CONDUIT AND/OR LESION COMPLIANCE, OPPOSITION FORCE AND INNER DIAMETER OF A BIOLOGICAL CONDUIT"; and U.S. patent application Ser. No. 14/801,269, "METHODS, DEVICES AND SYSTEMS FOR SENSING, MEASURING AND/OR CHARACTERIZING VESSEL AND/OR LESION COMPLIANCE AND/OR ELASTANCE CHANGES DURING VASCULAR PROCEDURES".

Various embodiments of the present invention address the issues, among others, discussed above.

DETAILED DESCRIPTION OF THE INVENTION

Figure 1:
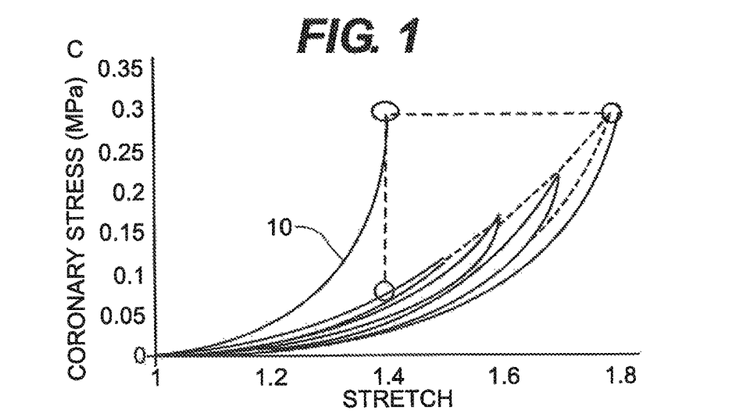
FIG. 1 is a graphic illustration of a typical stress strain curve of a single balloon inflation to the point where the artery wall tissue is damaged.

Various embodiments of the present invention are illustrated in the Figures. Thus, FIG. 1 is a graphic illustration comprising a reference line 10 illustrating the typical stress strain curve of a single balloon inflation procedure to the point where the artery wall is damaged. The remaining lines, and dots, illustrate how a pulsatile inflation/cyclically stretched pressure pulse period serially applied as described herein lowers the applied stress for a given strain on the artery wall and/or may be strained further at similar safe stress levels.

Figure 2:
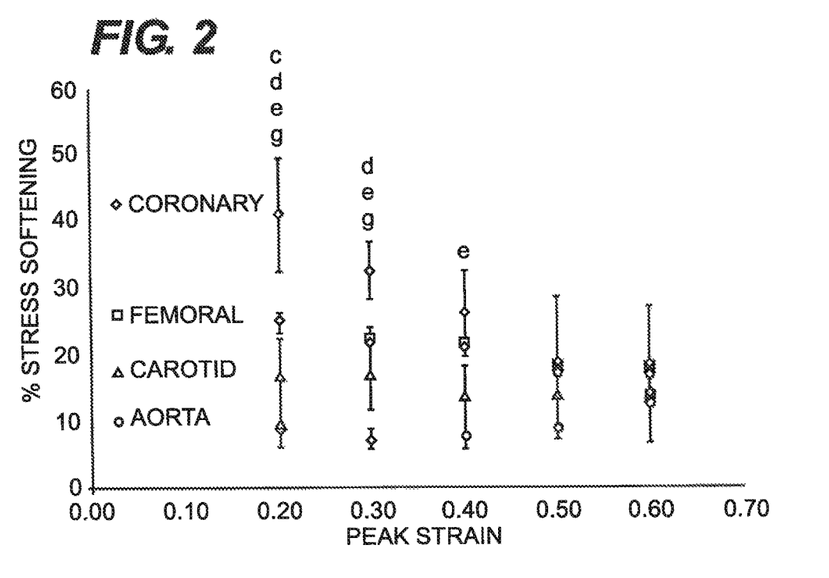
FIG. 2 is a graphic indicating that arteries with higher collagen content will be softened to a greater degree than arteries with lower collagen content.
Figure 3:
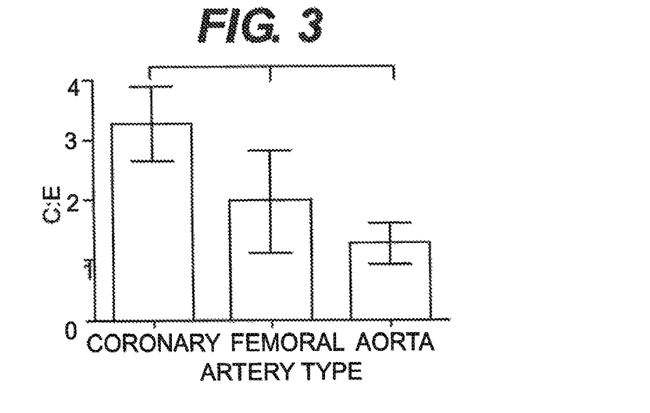
FIG. 3 is a graphic illustrating that different arteries have different collagen to elastin ratios.

FIG. 2 is a graphic indicating that arteries with higher collagen content will be softened to a greater degree than arteries with lower collagen content. FIG. 3 is a graphic illustrating that different arteries have different collagen to elastin ratios.

Figure 4:
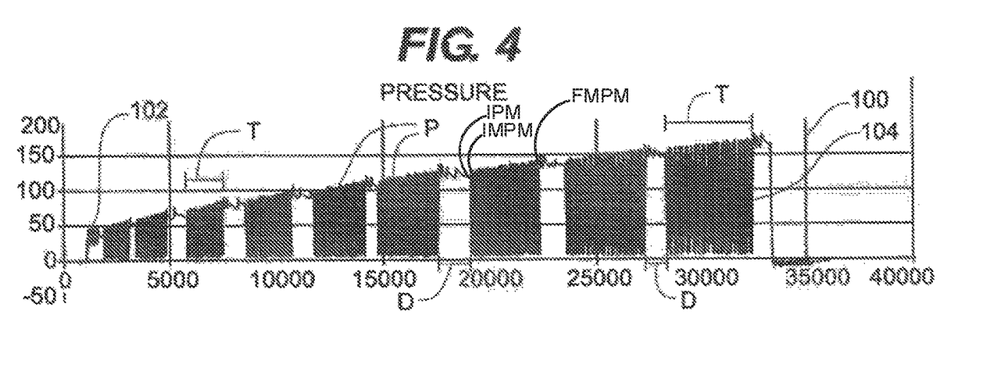
FIG. 4 is a pressure plot obtained using one embodiment of the present invention.

FIG. 4 is a pressure plot obtained using one embodiment of the present invention in a cadaver study. The method creates a successive series of pressure pulse periods with 40 steps per atmosphere wherein the velocity (strain rate) was set to a unit less number of 15. The steps may be modified to any number, e.g., 1 to 99 steps and the velocity may also be modified to any number, e.g., from 1 to 99.

Figure 5:
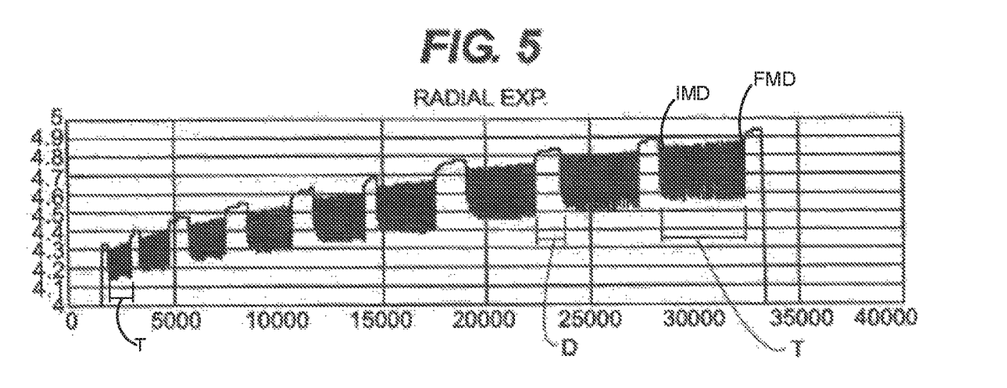
FIG. 5 is a graphic illustration of balloon diameter change in conjunction with the pressures employed in the embodiment of the present invention giving rise to the pressure plot of FIG. 4.

FIG. 5 is a graphic illustration of balloon diameter change in conjunction with the pressures employed in the embodiment of the present invention giving rise to the pressure plot of FIG. 4. The balloon diameter changes are driven by the material properties and will vary between manufacturers and models of the various known balloons.

Thus, certain embodiments of the present invention comprise a plurality of pressure pulse periods, with relaxation periods therebetween, delivered via a balloon placed within an occlusion within a biological conduit, e.g., a blood vessel such as an artery. Each pressure pulse period comprises a beginning timepoint with an initial minimum pressure magnitude and an ending timepoint with a final maximum pressure magnitude. The pressure pulse periods may increase, or vary, pressure magnitude within each pressure pulse period and/or may comprise a single magnitude pressure magnitude within each pressure pulse period. In addition, the time interval for each pressure pulse period may successively increase from an initial pressure pulse period time interval to a final pressure pulse period time interval, as shown in FIG. 5. Alternatively, the time intervals T for the pressure pulse period applications may be substantially equivalent in certain embodiments. Further, the pressure pulse periods may increase in magnitude from an initial pressure pulse period 102 to a final pressure pulse period 104 as is best illustrated in FIG. 4. In addition, the pressure magnitude within an individual pressure pulse period may be constant or may increase, or otherwise be variable. For example, each pressure pulse period may comprise a successively increasing plurality of pressure magnitudes between the initial minimum pressure magnitude and the final maximum pressure magnitude. An example of increasing pressure magnitude within individual pressure pulse periods is shown in FIGS. 4 and 5, with 5 illustrating the related radial expansion of the balloon as referenced by the y-axis. As shown in FIG. 4, each pressure pulse period may further comprise an initiation pressure magnitude adapted to initiate a successive pressure pulse period, with the initiation pressure magnitude being greater than zero and less than the final maximum pressure magnitude of the immediately preceding pressure pulse period in the series of pressure pulse periods. In such examples, the final maximum pressure magnitude increases across the series of pressure pulse periods (e.g with the final maximum pressure magnitude of at least one successive pulse period being greater than the final maximum pressure magnitude of each preceding pressure pulse period). In addition, the initial minimum pressure magnitude of at least one successive pulse period may be greater than the initial minimum pressure magnitude of each preceding pressure pulse period, as shown in FIG. 4.

Accordingly, and with reference to FIGS. 4, 5 and 8A-8D, a method according to certain embodiments of the present invention comprise a series 100 of pressure pulse periods P applied to the internal walls of a blood vessel over a period of time, each pressure pulse period P comprising a time T that may be constant or may vary, e.g., increase with each successive pressure pulse period P within the series of pressure pulse periods 100. Each pressure pulse period P may comprise at least one pressure wave form, a pressure magnitude or magnitudes within each individual pressure wave form and/or across the pressure pulse period comprising one or more pressure wave forms. The pressure magnitude is represented in FIG. 4 by the y-axes, with time on the x-axis. The pressure magnitude for each pressure wave form may be constant within the wave form or may vary, e.g., may increase with time. Alternatively, or in combination with the pressure magnitude, the balloon's radial expansion may be a further element of the pressure pulse period(s) as illustrated by the y-axis in FIG. 5, as defined by an initial minimum diameter (IMD) and a final maximum diameter (FMD) for the balloon during each pressure pulse period. Further, each pressure wave form may comprise a time of pressuring 102 that may be constant or that may vary across the pressure wave forms of the series of pressure pulse periods. Moreover, a decompression period between each successive or adjacent pressure wave forms D is provided to allow the vessel material time to relax and realign. As illustrated in FIG. 4, a decompression period between successive pressure pulse periods may comprise at least one pressure magnitude that is greater than zero. The length in time of the decompression periods may be equal through the series of pressure pulse periods or may be variable. Finally, with particular reference to FIGS. 8A-8D, the velocity of the pressure increase, i.e., balloon inflation, at the beginning of an individual pressure pulse period, and the velocity of the pressure decrease, i.e., balloon deflation, at the end of an individual pressure pulse period are significant elements of the series of pressure pulse periods.

It will be understood that the series of pressure pulse periods 100, and all elements and variables comprising the series of pressure pulse periods 100 may be predetermined and executed using a controller comprising a processor capable of executing programmed instructions that, when executed, result in a balloon expansion regimen that follows the series of pressure pulse periods 100.

Examples of pressure pulse period series 100 are provided in FIGS. 4, 5 and 8A-8D. FIGS. 8A-8D illustrate some exemplary wave forms that may be used to achieve the intended results of the present invention. However, pulses, velocities and waveforms used in various embodiments of the present invention may vary, as shown in FIGS. 8A-8D. For example, wave forms may be non-variable in shape, for example a repeating constant pressure such as a sine wave of constant peak magnitude and period (time), or may be variable, i.e., with varying pressure and/or period. In addition, the pressure waveform types may be the same, e.g., all sine waves, within a particular pressure pulse period P, or the waveforms may vary within a pressure pulse period P, e.g., sine waves alternating with square waves and/or triangle waves or saw tooth waves as the skilled artisan will readily recognize. Similarly, the waveform types may be constant, or may vary across the series of pressure pulse periods 100 so that one pressure pulse period P in the series of pressure pulse periods 100 employs square waves and a second pressure pulse period P in the series of pressure pulse periods 100 employs saw tooth waves. The skilled artisan will recognize equivalents of these parameters, all of which are within the scope of the present invention.

Thus, the balloon outer diameter is systematically increased and decreased, at specified velocities, by predetermined specific pressure increments over predetermined time intervals. The exemplary vessel, e.g., arterial, wall is given time to relax between each pressure pulse period application. The cyclic nature of longer and longer strains through each successive pressure pulse period as shown in FIGS. 4 and 5 causes weaker short chains of vessel wall material to disengage giving the longer and more entangled chains of vessel wall material time to align and conform to the strain being applied in a way that causes less overall vessel wall material chain breakage and resulting tissue damage. Stated differently, the pressure magnitude for each pressure pulse period is selected so as to not deform the subject vessel wall non-elastically. Because a preferred embodiment of the present invention comprises an incremental increase in at least one of the variable elements, e.g., pressure magnitude, time of pressure application, velocity of pressure, etc., the vessel wall is allowed to adapt to the increasing load without deformation while the balloon breaks up calcified material.

Because the longer and more entangled vessel wall material chains are not broken or damaged, the exemplary artery may be strained further at safe stress levels, or the artery may be strained to similar pressure levels as known angioplasty methods, but with lower stress levels placed on the vessel wall over the length of the inventive procedure, resulting in lower overall vessel wall material chain/tissue damage.

In addition to the stress softening advantages with reduction of tissue damage, including reduction in cell injury responses, there is another benefit. That is, the expanded section of conduit, e.g., a blood vessel such as an artery, that has been stress softened will have increased compliance. This, in turn, results in healthy normal conduit, e.g., artery, compliance with normal blood pressure returning to the previously compromised artery.

Figure 6:
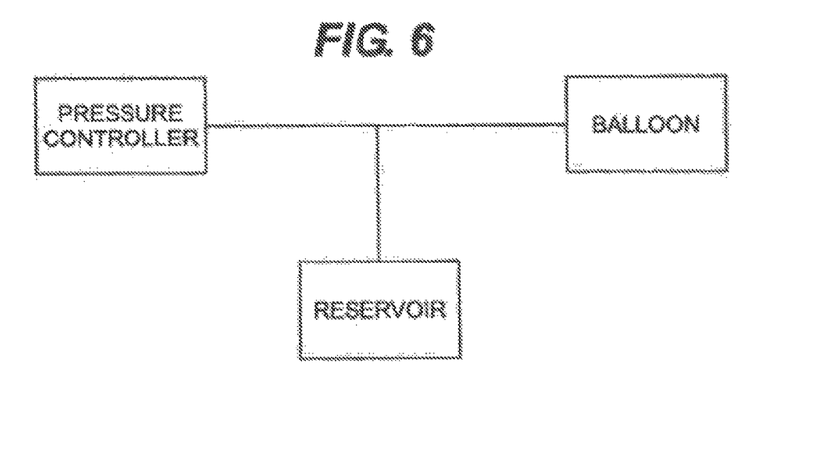
FIG. 6 illustrates a schematic view of one embodiment of the present invention.

FIG. 6 illustrates an exemplary system for implementing the pressure pulse periods of the various embodiments of the present invention. Thus, a pressure controller having programmed instructions therein and/or otherwise adapted to provide the pressure pulse periods in a predetermined sequence as described above is provided. The pressure controller is operatively connected, either wired or wirelessly, to a fluid reservoir and to a known balloon capable of fluid inflation from the reservoir according to the instructions provided by the pressure controller.

The functionality of the above method may be achieved using a variety of devices including as shown in FIG. 6. Alternatively, as in FIG. 7, the system may comprise a balloon of known elasticity, or compliance, a device, e.g., a syringe, that is capable of injecting a known and fixed volume of fluid to inflate the balloon to the required pressure pulse period requirements, an optional pressure transducer in operative communication and connection with the inflating balloon to measure the pressure experienced by the balloon as it inflates. There is illustrated an exemplary linear motor that is capable of translating the plunger of syringe to meet the pressure pulse period requirements. A pressure transducer, when present, is in operative communication and connection with the balloon to measure and display and/or record the pressure data as well as the corresponding volume data.

Figure 7:
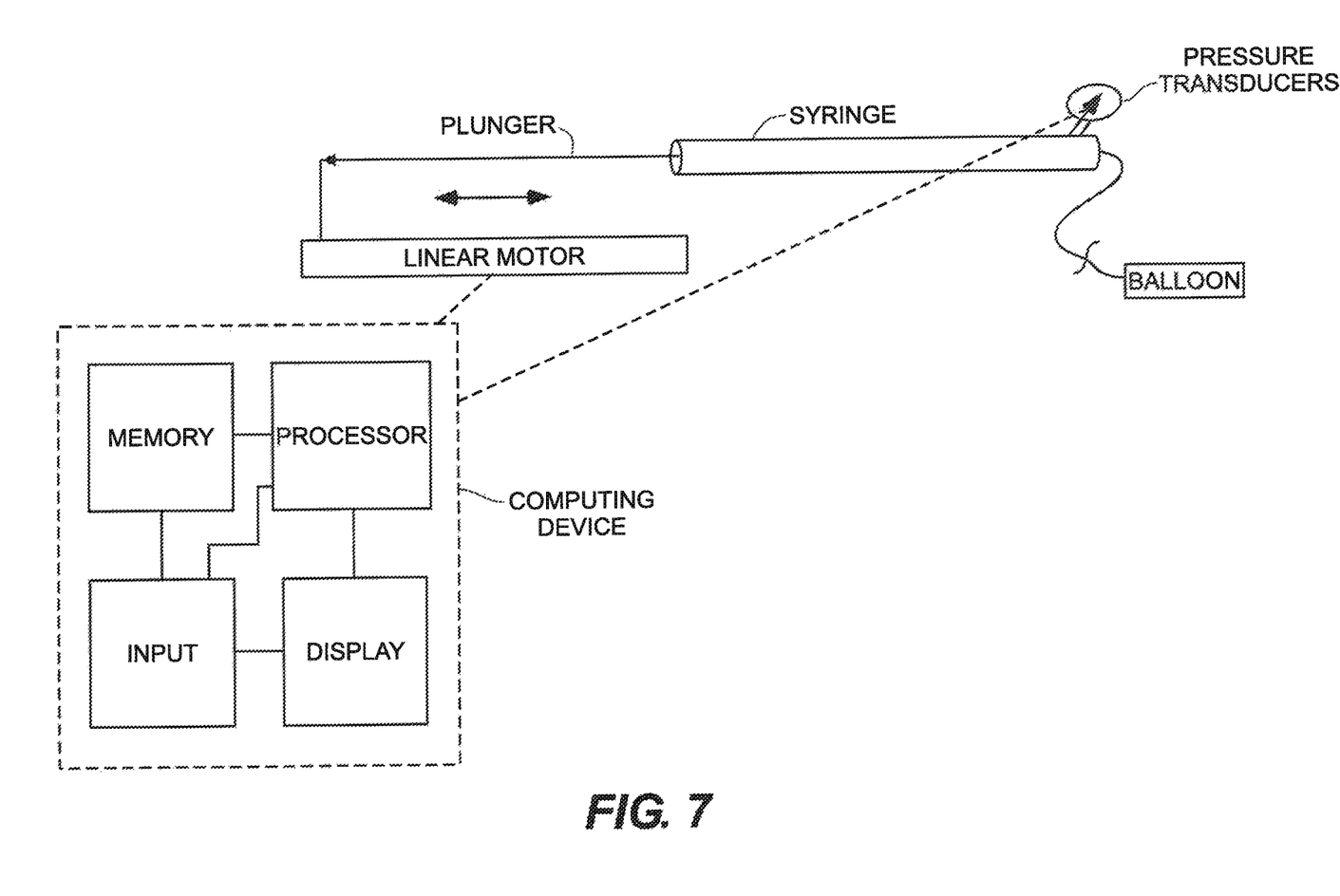
FIG. 7 illustrates a schematic view of one embodiment of the present invention.
Figure 8A:
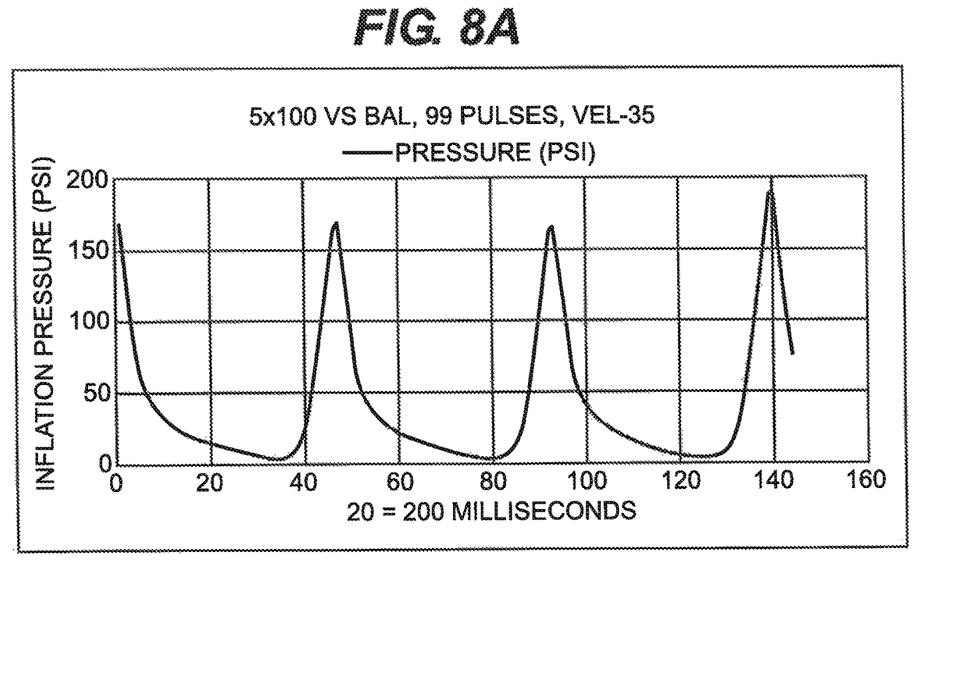
FIGS. 8A-8D illustrate pressure and diameter plots, respectively, as well as pulse counts for embodiments of the present invention.
Figure 8B:
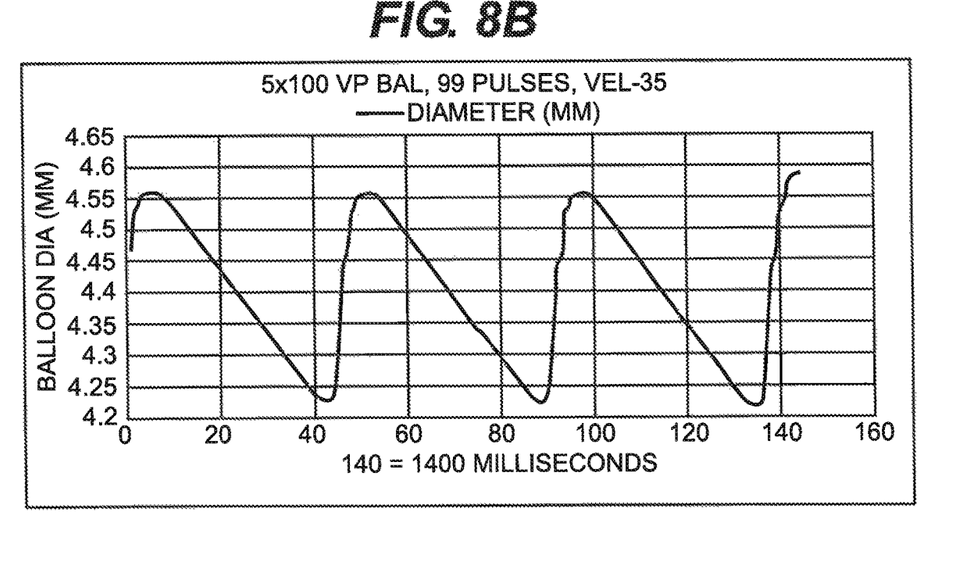
Figure 8C:
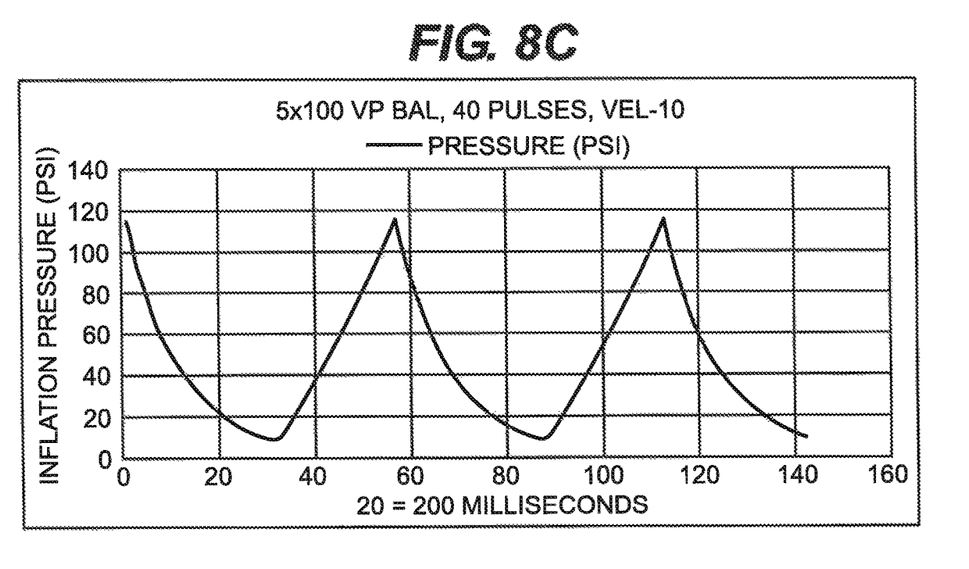
Figure 8D:
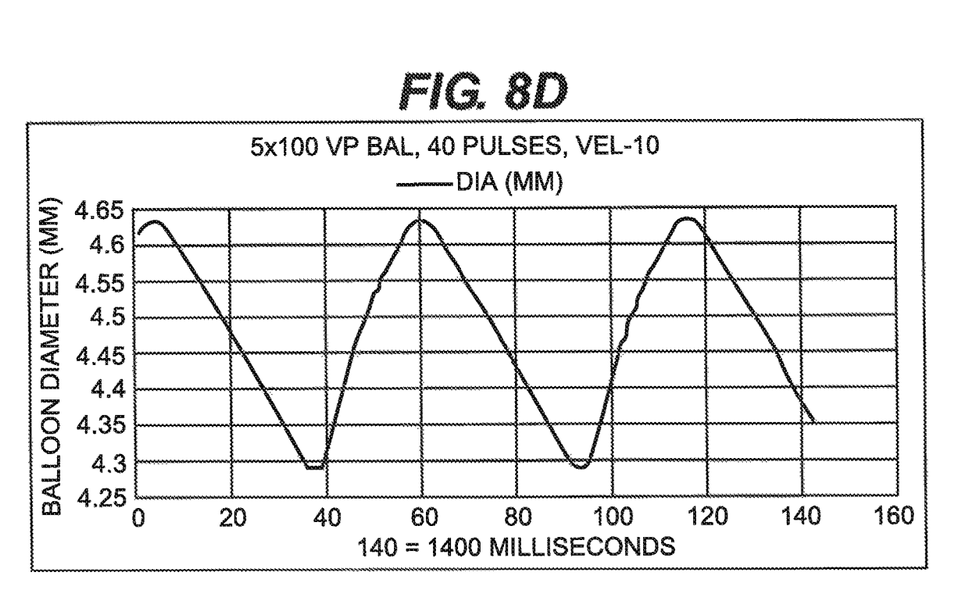

The system of FIG. 7 is shown in operative communication with an external computing device comprising a memory in communication with a processor and an input, e.g., keyboard that is also in operative communication with the processor and a display which is, in turn, in operative communication with the processor. As the skilled artisan will recognize, the memory may store programmed instructions for the series of pressure pulse periods 100 and the processor may be adapted to execute the stored programmed instructions.

Still more alternatively, a pressure controller that functions in a manner similar to a speaker coil in order to change the pressure wave form at a wider/higher range of frequencies with a wide amplitude range and with more precision may be employed to generate the desired pressure pulse periods of the present invention.

Various embodiments of the present invention may comprise a combination of the incrementally pulsed balloon inflation forces described herein with a balloon that is at least partially covered with a wire, wherein the wires create a series of high stress regions, or risers, that move with the balloon surface as it expands and contracts. When the at least partially wire-covered balloon is inflated, the wire contact pressures increase sharply along with the artery wall becoming less compliant as it is stretched in response to the radial expansion of the balloon. Any rigid sections within the artery wall will be broken into smaller pieces. As these rigid sections are broken into smaller segments, the tissue between and surrounding the smaller rigid sections will begin to stretch in response to the radially expanding balloon. Without the incremental stress softening of the tissue around a rigid section provided by the various embodiments of the present invention, the tissue would experience high strain rates and will likely be torn or damaged, resulting in arterial wall injury.

The methods described herein may be used on any known percutaneous transluminal angioplasty (PTA), percutaneous transluminal coronary angioplasty (PTCA), stent delivery system, specialty balloons or CSI BOSS application.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A method for treating an at least partially calcified occlusion in a blood vessel, comprising:
    providing an inflatable balloon;
    providing a fluid reservoir in operative communication with the inflatable balloon; and
    providing a pressure controller in operative communication with the fluid reservoir and adapted to deliver fluid from the fluid reservoir to the balloon in a series of pressure pulse periods;
    executing a series of balloon inflations and partial deflations comprising the series of pressure pulse periods, each pressure pulse period in the series comprising the following predetermined parameters:
        a beginning timepoint with an initial minimum pressure magnitude and an ending timepoint with a final maximum pressure magnitude;
        a successively increasing plurality of pressure magnitudes between the initial minimum pressure magnitude and the final maximum pressure magnitude;
        a decompression period between successive pressure pulse periods comprising at least one pressure magnitude, wherein each of the at least one pressure magnitude of the decompression period is greater than zero; and
        an initiation pressure magnitude adapted to initiate a successive pressure pulse period, wherein the initiation pressure magnitude is greater than zero and less than the final maximum pressure magnitude of the immediately preceding pressure pulse period in the series of pressure pulse periods,
    wherein the final maximum pressure magnitude increases across the series of pressure pulse periods.

2. The method of claim 1, wherein the initial minimum pressure magnitude of each pressure pulse period is subsequent to the initiation pressure magnitude of that pressure pulse period, and wherein the initial minimum pressure magnitude of at least one successive pressure pulse period is greater than the final maximum pressure magnitude of the immediately preceding pressure pulse period.

3. The method of claim 2, wherein the initial minimum pressure magnitude of at least one successive pulse period is greater than the initial minimum pressure magnitude of each preceding pressure pulse period.

4. The method of claim 2, wherein the final maximum pressure magnitude of at least one successive pulse period is greater than the final maximum pressure magnitude of each preceding pressure pulse period.

5. The method of claim 1, wherein the pressure pulse period for each successive pressure pulse period within the series of pressure pulse periods increases in time.

6. The method of claim 1, wherein the decompression period between successive pressure pulse periods comprises a time period that is constant.

7. The method of claim 1, wherein the decompression period between successive pressure pulse periods comprises a time period that is variable.

8. The method of claim 1, wherein the decompression period between successive pressure pulse periods comprises a time period that increases across the series of pressure pulse periods.

9. The method of claim 1, wherein the predetermined parameters of each pressure pulse period further comprise at least one waveform type that does not change within each pressure pulse period or across the series of pressure pulse periods.

10. The method of claim 1, wherein the predetermined parameters of each pressure pulse period further comprise at least one waveform type that changes within at least one of the pressure pulse periods within the series of pressure pulse periods.

11. The method of claim 1, wherein the predetermined parameters of each pressure pulse period further comprise a pressure velocity at the initiation of the pressure pulse period, and wherein the pressure velocity at the initiation of each of the pressure pulse periods within the series of pressure pulse periods is constant and does not vary between pressure pulse periods.

12. The method of claim 1, wherein the predetermined parameters of each pressure pulse period further comprise a pressure velocity at the initiation of the pressure pulse period, and wherein the pressure velocity at the initiation of each of the pressure pulse periods within the series of pressure pulse periods increases with each successive pressure pulse period.

13. The method of claim 1, wherein, for each of the pressure pulse periods, the inflatable balloon defines:
   an initial minimum diameter corresponding to the initial minimum pressure magnitude of that pulse period; and
   a final maximum diameter corresponding to the final maximum pressure magnitude of that pulse period.

14. The method of claim 13, wherein the initial minimum diameter of the balloon during at least one successive pressure pulse period is greater than the final maximum diameter of the balloon during the immediately preceding pressure pulse period.

15. The method of claim 13, wherein at least the initial minimum diameter of the balloon during at least one successive pulse period is greater than the initial minimum diameter of the balloon during each preceding pressure pulse period.

16. The method of claim 13, wherein at least the final maximum pressure diameter of the balloon during at least one successive pulse period is greater than the final diameter of the balloon during each preceding pressure pulse period.

* * * * *